United States Patent
Nomura (10) Patent No.: US 9,625,288 B2
(45) Date of Patent: Apr. 18, 2017

(54) MOTION ANALYSIS SYSTEM AND MOTION ANALYSIS METHOD

(71) Applicant: Seiko Epson Corporation, Tokyo (JP)

(72) Inventor: Kazuo Nomura, Shiojiri (JP)

(73) Assignee: Seiko Epson Corporation (JP)

( * ) Notice: Subject to any disclaimer, the term of this patent is extended or adjusted under 35 U.S.C. 154(b) by 928 days.

(21) Appl. No.: 13/741,662

(22) Filed: Jan. 15, 2013

(65) Prior Publication Data

US 2013/0191063 A1 Jul. 25, 2013

(30) Foreign Application Priority Data

Jan. 24, 2012 (JP) .................................. 2012-011679

(51) Int. Cl.
| | | |
|---|---|---|
| *G01R 35/00* | (2006.01) | |
| *G01D 18/00* | (2006.01) | |
| *G06F 17/00* | (2006.01) | |
| *G01P 1/12* | (2006.01) | |
| *A61B 5/00* | (2006.01) | |
| *A61B 5/11* | (2006.01) | |

(52) U.S. Cl.
CPC ............ *G01D 18/00* (2013.01); *A61B 5/1121* (2013.01); *A61B 5/1128* (2013.01); *A61B 5/6895* (2013.01); *G01P 1/12* (2013.01); *G06F 17/00* (2013.01)

(58) Field of Classification Search
CPC ......... G01P 1/127; G01P 1/12; A63B 24/0003
USPC ........................................................... 702/89
See application file for complete search history.

(56) References Cited

U.S. PATENT DOCUMENTS

| | | | | |
|---|---|---|---|---|
| 3,794,773 A | * | 2/1974 | Jacob et al. ................... | 370/304 |
| 2002/0114493 A1 | * | 8/2002 | McNitt et al. ................. | 382/107 |
| 2005/0223799 A1 | * | 10/2005 | Murphy .......................... | 73/510 |

FOREIGN PATENT DOCUMENTS

| | | |
|---|---|---|
| JP | 2008-073210 | 4/2008 |
| JP | 2008-271383 | 11/2008 |
| JP | 2010-016576 | 1/2010 |
| JP | 2011-055123 | 3/2011 |
| JP | 2011-155957 | 8/2011 |

* cited by examiner

*Primary Examiner* — John Breene
*Assistant Examiner* — Stephanie Bloss
(74) *Attorney, Agent, or Firm* — Harness, Dickey & Pierce, P.L.C.

(57) ABSTRACT

A motion analysis system includes first to N-th (N is an integer of 2 or more) sensor units which is attached to an object, an analysis unit which obtains a plurality of items of sampling data output from the sensor units, to analyze a motion of the object, a synchronization signal sending unit which transmits a first synchronization signal group including N first synchronization signals in order from the first to the N-th sensor unit, and transmits a second synchronization signal group including N second synchronization signals in order from the N-th to the first sensor unit, with respect to sensor unit, and a reference synchronization signal generation unit which generates a reference synchronization signal which is to be a reference with respect to the first to N-th sensor units, based on the first and second synchronization signal groups received by sensor unit.

5 Claims, 8 Drawing Sheets

| | X | Y | Z |
|---|---|---|---|
| 0 | | | |
| 0 | | | |
| 0 | | | |
| 0 | | | |
| 1 | | | |
| 0 | | | |
| 0 | | | |
| 0 | | | |
| 0 | | | |

23g

| | X | Y | Z |
|---|---|---|---|
| 0 | | | |
| 0 | | | |
| 0 | | | |
| 0 | | | |
| 1 | | | |
| 0 | | | |
| 0 | | | |
| 0 | | | |
| 0 | | | |

23h

| | X | Y | Z |
|---|---|---|---|
| 0 | | | |
| 0 | | | |
| 0 | | | |
| 0 | | | |
| 1 | | | |
| 0 | | | |
| 0 | | | |
| 0 | | | |
| 0 | | | |

22g

| | | X | Y | Z |
|---|---|---|---|---|
| DATA(1) | 1 ← REFERENCE SYNCHRONIZATION FLAG | | | |
| DATA(2) | 0 | | | |
| DATA(3) | 0 | | | |
| DATA(4) | 0 | | | |
| DATA ... | 1 | | | |
| DATA(k-3) | 0 | | | |
| DATA(k-2) | 0 | | | |
| DATA(k-1) | 0 | | | |
| DATA(k) | 0 | | | |

MOTION ANALYSIS SYSTEM AND MOTION ANALYSIS METHOD

BACKGROUND

1. Technical Field

The present invention relates to a motion analysis system and a motion analysis method which analyze a motion of an object such as a golf swing or the like.

2. Related Art

As a method of evaluating a motion of an object such as a golf swing, an image captured by a camera has limited analysis information. Thus, it is proposed to analyze the swing by providing a plurality of sensors such as acceleration sensors, Gyro sensors, and the like on a golf club as disclosed in JP-A-2008-73210.

A plurality of sensors are attached onto an object for analyzing motion of the object. In JP-A-2008-73210, Gyro sensors and acceleration sensors are attached onto a shaft portion and a head portion of a golf club.

As described above, in order to analyze motion of an object based on output from the plurality of sensors attached to the object, it is necessary to synchronize the time of the output from the plurality of sensors. This is because it is necessary to acquire information of the same time or the same position of the object from the plurality of sensors.

At this time, when a synchronization signal is transmitted from a host terminal to the plurality of sensors in chronological order, for example, since the time to receive the synchronization signal for the plurality of sensors is shifted, it is difficult to precisely synchronize the time of the output from the plurality of sensors.

SUMMARY

An advantage of some aspects of the invention is to provide a motion analysis system and a motion analysis method which can reliably synchronize time of output from a plurality of sensors even when synchronization signals are transmitted to the plurality of sensors in chronological order.

(1) An aspect of the invention is directed to a motion analysis system including: first to N-th (N is an integer equal to or larger than 2) sensor units which includes a reception unit of a synchronization signal and a sensor and is attached to an object; an analysis unit which obtains a plurality of items of sampling data output from the first to N-th sensor units, to analyze a motion of the object; a synchronization signal sending unit which transmits a first synchronization signal group including N first synchronization signals in order from the first sensor unit to the N-th sensor unit, and transmits a second synchronization signal group including N second synchronization signals in order from the N-th sensor unit to the first sensor unit, with respect to the reception unit which is provided in the first to N-th sensor units; and a reference synchronization signal generation unit which generates a reference synchronization signal which is to be a reference with respect to the first to N-th sensor units, based on the first synchronization signal group and the second synchronization signal group received by the reception unit which is provided in the first to N-th sensor units.

In the aspect of the present invention, the reception unit provided in the first to N-th sensor units receives two synchronization signals of N first synchronization signals in the first synchronization signal group and N second synchronization signals in the second synchronization signal group. At this time, the first sensor unit receives one of N first synchronization signals in the forward direction initially, and receives one of N second synchronization signals in the backward direction finally. Meanwhile, the N-th sensor unit receives one of N first synchronization signals in the forward direction finally, and receives one of N second synchronization signals in the backward direction initially. Thus, in the first to N-th sensor units, it is possible to set the intermediate times obtained by bisecting the intervals of the receiving times of two synchronization signals received by reception unit to be substantially equivalent. The reference synchronization signal generation unit can generate the reference synchronization signal based on two synchronization signals received by the reception unit of the first to N-th sensor units. The analysis unit can extract the data of the same time from the plurality of sampling data items obtained from the first to N-th sensor units, and can analyze the angular velocity, the acceleration, the velocity, the position and the like at the same time with respect to the plurality of the locations of the object based on the reference synchronization signal. In addition, any one may be transmitted first regardless of transmitting order of the first synchronization signal group and the second synchronization signal group.

(2) The aspect of the invention may be configured such that, in the first synchronization signal group and the second synchronization signal group, points plotted as sending times on a time axis are line-symmetric with respect to a line orthogonal to the time axis which passes a point obtained by bisecting an interval between the first synchronization signal group and the second synchronization signal group.

With this configuration, line-symmetry of the first and second synchronization signal groups at the time of transmission also reflects the first and second synchronization signal groups at the delayed time of reception. Thus, the reference synchronization signal generation unit can set the intermediate times obtained by bisecting the intervals of the receiving times of two synchronization signals received by reception unit to be substantially equivalent to the time at the point obtained by bisecting the interval of the first synchronization signal group and the second synchronization signal group. Accordingly, the reference synchronization signal generated by the reference synchronization signal generation unit can be substantially set to be equivalent with respect to the sampling data from the first to N-th sensor units.

(3) The aspect of the invention may be configured such that a sending interval between n-th ($1 \leq n \leq N-1$) and (n+1)-th synchronization signals of the first synchronization signal group and a sending interval between (N−n)-th and [N−(n−1)]-th synchronization signals of the second synchronization signal group are equivalent to each other.

Accordingly, the above-described line-symmetry of the first and second synchronization signal groups can be secured. That is, each synchronization signal of the first and second synchronization signal groups may be transmitted at given intervals, or the intervals may be different from each other as long as the line-symmetry is secured.

(4) The aspect of the invention may be configured such that the reference synchronization signal generation unit generates the reference synchronization signal at intermediate times which are obtained by bisecting intervals of receiving time of the first synchronization signals and the second synchronization signals received by the reception unit which is provided in the first to N-th sensor units.

As described above, in the first to N-th sensor units, since the intermediate time obtained by bisecting intervals of receiving times of two synchronization signals received by reception unit can be set to be substantially equivalent, it is preferable to generate the reference synchronization signal at the intermediate time thereof.

(5) The aspect of the invention may be configured such that the synchronization signal sending unit sends a plurality of pairs of synchronization signal groups when setting the first synchronization signal group and the second synchronization signal group as a pair of synchronization signal groups, and the reference synchronization signal generation unit generates the reference synchronization signal at an average intermediate time obtained by averaging the plurality of intermediate times which are obtained from pair of synchronization signal groups from the plurality of pairs of the synchronization signal groups. Thus, it is possible to precisely improve the reference synchronization signal.

(6) The aspect of the invention may be configured such that a host terminal to which the output from the first to N-th sensor units is input is provided, the analysis unit and the reference synchronization signal generation unit are provided in the host terminal, a data processing unit are provided in the plurality of sensor units, and the data processing unit outputs a plurality of sampling data items which are obtained by sampling the output from the sensor in chronological order, and synchronization flags set to two sampling data items which are obtained by sampling at the time of sampling corresponding to the time of receiving the first synchronization signal and the second synchronization signal from the plurality of sampling data items.

Thus, each processing unit of the plurality of sensor units is only necessary to set the synchronization flag to two sampling data items specified based on two synchronization signals, and other processes can be executed as the process in the host terminal.

(7) The aspect of the invention may be configured such that the reference synchronization signal generation unit sets a reference synchronization flag with respect to the plurality of sampling data items obtained from the first to N-th sensor units, which is sampling data corresponding to a center position of two sampling data items set with the synchronization flags.

As described above, a process of calculating from the receiving time of the synchronization signal is not necessary, and the reference synchronization signal generation unit can specify a data position at which the reference synchronization flag is allocated from two synchronization flags. In addition, if total data number k of two sampling data items and the data therebetween is an odd number, the center position between two sampling data items is definitely determined to be in a [(k+1)/2]-th position, and if the total data number k is an even number, the center position can be any one of (k/2)-th and [(k+2)/2]-th center data.

(8) The aspect of the invention may be configured such that the reference synchronization signal generation unit is provided in the plurality of sensor units, the plurality of sensor units further includes a data processing unit, the data processing unit outputs the plurality of sampling data obtained by sampling the output of the sensor in chronological order, and the reference synchronization flag which is one of the plurality of sampling data items, and which is set to the sampling data corresponding to the time of sampling corresponding to the reference synchronization signal.

As described above, when the reference synchronization signal generation unit is provided in the plurality of sensor units, instead of the synchronization flag described above, it is possible to set the reference synchronization flag to one of the plurality of sampling data items to be output. At this time, since data, subsequent to the data to which the reference synchronization flag is set, is output, it is not necessary to transmit unnecessary data to the host terminal.

(9) Aspect of the invention is directed to a motion analysis method for obtaining a plurality of sampling data items output from first to N-th (N is an integer equal to or larger than 2) sensor units attached to an object, to analyze a motion of the object, the method including: transmitting a first synchronization signal group including N first synchronization signals in order from the first sensor unit to the N-th sensor unit, and transmitting a second synchronization signal group including N second synchronization signals in order from the N-th sensor unit to the first sensor unit, with respect to the reception unit which is provided in first to N-th sensor units; and generating a reference synchronization signal which is to be a reference with respect to the first to N-th sensor units, based on the first synchronization signal group and the second synchronization signal group received by the reception unit which is provided in first to N-th sensor units.

According to this another aspect of the invention, in the same manner as the aspect of the invention described above, the reference synchronization signal may be allocated on one of the plurality of sampling data items output from first to N-th sensor units.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the present invention will be described in detail. The embodiments which will be described later do not particularly limit the content of the invention disclosed in the aspects, and all of the configurations which will be described in the embodiments are not limited to be as the means for solving the invention.

1. Outline of Motion Analysis System

Figure 1:
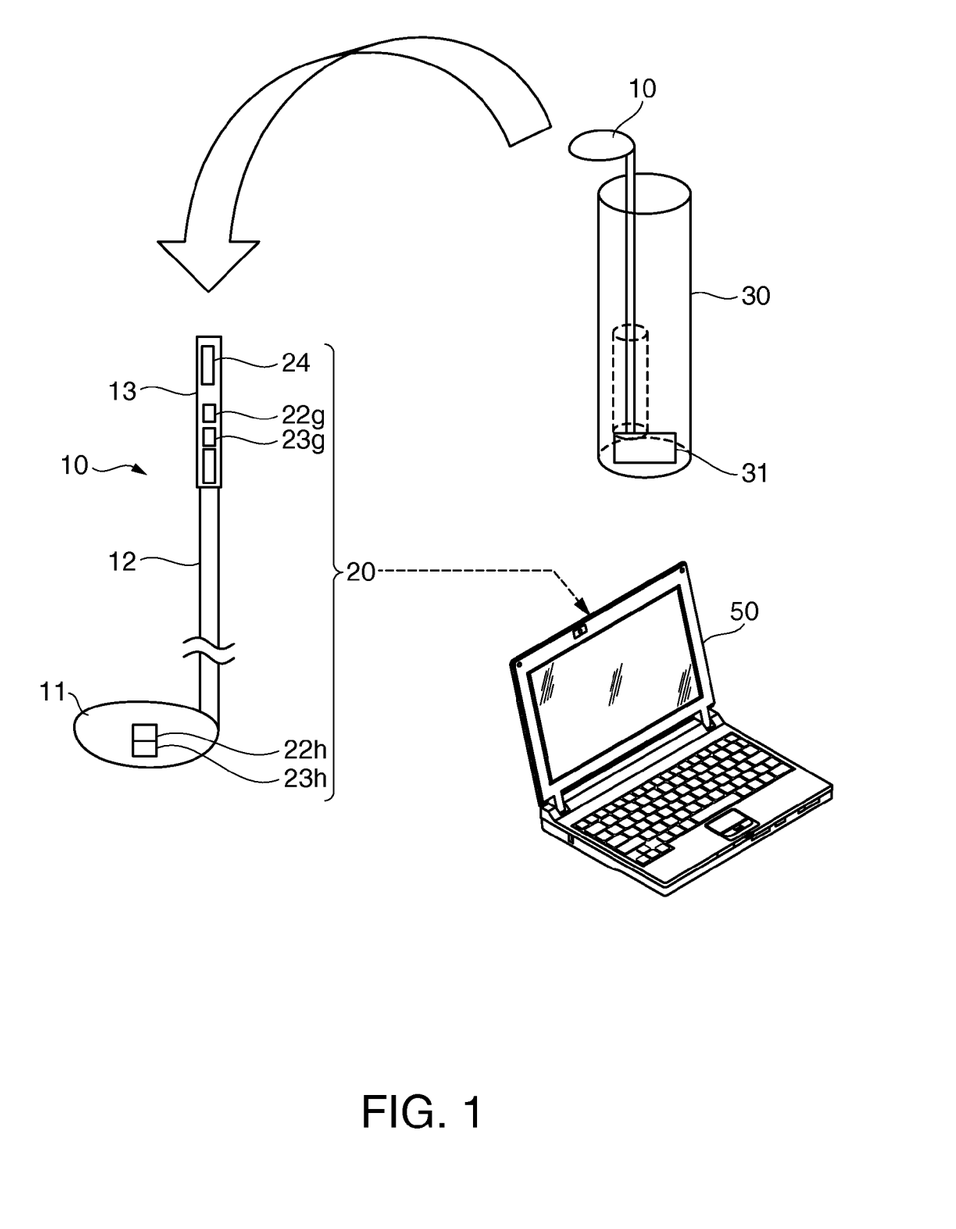
FIG. 1 is a schematic perspective view of a motion analysis device according to an embodiment of the present invention.

FIG. 1 is a schematic configuration view of a swing analysis system (motion analysis system) of a golf club (object or exercise equipment) to which one embodiment of the invention is applied. As shown in the drawing, the swing analysis system includes a sensor unit group 20 provided in the golf club 10 and a host terminal 50. The host terminal 50 is a personal computer, for example.

The club 10 includes a sensor unit group 20 for detecting behaviors of the club 10 at the time of the swing. However, the appearance, weight, center and the like thereof are designed so as to be the same as the typical golf club.

The sensor unit group 20 attached to the club 10 includes N units (N is an integer equal to or larger than 2), for example, four sensor units 22h, 22g, 23h, and 23g. Two sensor units 22h and 22g are Gyro sensor units, for example. The Gyro sensor units 22h and 22g detect angular velocity in a triaxial (x, y, and z) direction with a triaxial Gyro sensor. The Gyro sensor unit 22h and the Gyro sensor unit 22g are embedded in a head portion 11 of the club 10 and in a grip portion 13 of the club 10, respectively. The Gyro sensor is a micro Gyro sensor in a triaxial vibration type, for example.

Other two sensor units 23h and 23g are acceleration sensor units, for example. The acceleration sensors included in each of the acceleration sensor units 23h and 23g detect rates of acceleration in a triaxial (x, y, and z) direction, with a triaxial acceleration sensor. The acceleration sensor unit 23h and the acceleration sensor unit 23g are embedded in the head portion 11 of the club 10 and in the grip portion 13 of the club 10, respectively. The acceleration sensor is a micro acceleration sensor of a triaxial vibration type, for example.

In addition, the plurality of sensor units are disposed at a position different from the object. Each sensor is disposed on the grip portion 13 and the head portion 11 in the embodiment is for a consideration of bending or torsion of a shaft 12 at the time of swing. By disposing each sensor on the grip portion 13 and the head portion 11 of which the positional relationship changes due to bending or torsion, it is possible to precisely detect the behavior of the golf club 10 at the time of the swing.

A storage battery 24 provided in the club 10 is a rechargeable battery, and is charged by a battery charger 31 provided in the club bag 30. A charging method can be set as a non-contact electric power supply method in which a point of contact is not necessary. Accordingly, an electrical passive device is provided for charging. In the club bag 30, since the club 10 is accommodated with the grip portion 13 to be at the bottom, the passive device is provided in the grip portion 13. When the club 10 is accommodated in the club bag 30, the electricity is automatically supplied to the passive device and the storage battery 24 is charged.

Figure 2:
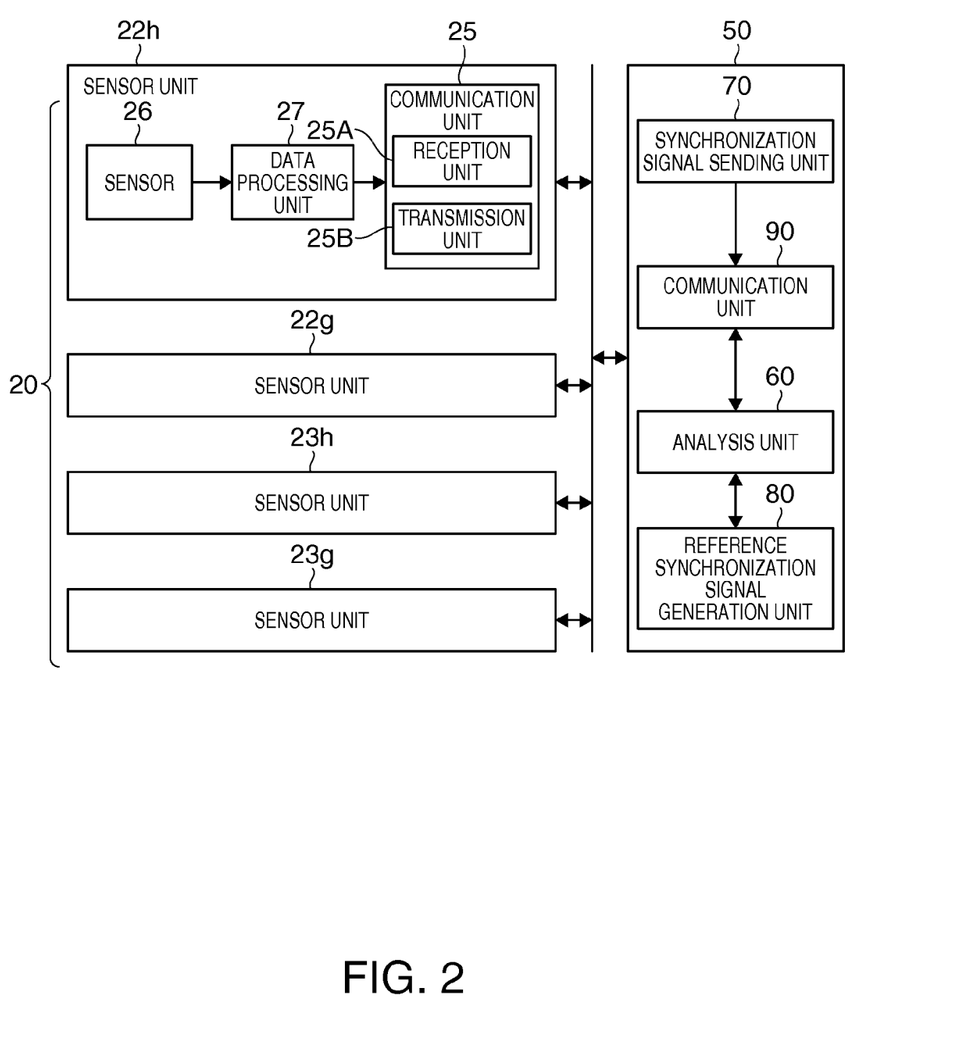
FIG. 2 is a schematic block diagram of a motion analysis device.

FIG. 2 is a schematic block diagram of the motion analysis system. In FIG. 2, each of the sensor units 22h, 22g, 23h, and 23g can include a communication unit 25 including a reception unit 25A of a synchronization signal and a transmission unit 25B of data, a sensor 26, and a data processing unit 27. The sensor 26 can be set as the triaxial Gyro sensor or the triaxial acceleration sensor described above. The data processing unit 27 obtains a plurality of sampling data items X(t), Y(t), and Z(t) which are obtained by sampling the output from the sensor 26 at a predetermined sampling frequency. The data processing unit 27 can allocate synchronization flags based on the synchronization signal received by the communication unit 25 to two sampling data items, for example.

Meanwhile, an analysis unit 60, a synchronization signal sending unit 70, a reference synchronization signal generation unit 80, and a communication unit 90 can be provided in the host terminal 50.

The analysis unit 60 obtains the plurality of sampling data items to be output from each communication unit 25 of the sensor units 22h, 22g, 23h, and 23g through the communication unit 90 to analyze the swing of the golf club 10. By performing time integration of angular velocity obtained from the Gyro sensor units 22h and 22g, the analysis unit 60 can detect an angle An(t) of the head portion 11 and the grip portion 13. By performing time integration of acceleration data Ac(t) obtained from the acceleration sensor units 23h and 23g, the analysis unit 60 can detect velocity V(t) and a position P(t) of the head portion 11 and the grip portion 13.

The synchronization signal sending unit 70 transmits the synchronization signal with respect to each reception unit 25 of the sensor units 22h, 22g, 23h, and 23g in chronological order through the communication unit 90. The reference synchronization signal generation unit 80 generates a reference synchronization signal to be reference with respect to the sensor units 22h, 22g, 23h, and 23g, based on the synchronization signal received by each communication unit 25 of the sensor units 22h, 22g, 23h, and 23g. In the embodiment, the reference synchronization signal generation unit 80 can set a reference synchronization flag with respect to each of the plurality of sampling data items obtained from each of the sensor units 22h, 22g, 23h, and 23g through the communication unit 90 and the analysis unit 60, which is sampling data corresponding to a center position of two sampling data items set with the synchronization flags.

In addition, the communication unit 25 of the sensor units 22h, 22g, 23h, and 23g and the communication unit 90 of the host terminal 50 are wirelessly connected to each other preferably using the Bluetooth standard. However, the communication units may be connected to each other with a wire depending on type of an object to which sensor units are attached.

In an example shown in FIG. 2, the synchronization signal sending unit 70 and the reference synchronization signal generation unit 80 are provided in the host terminal 50 shown in FIG. 1 in addition to the analysis unit 60 and the communication unit 90; however, it is not limited thereto. That is, the synchronization signal sending unit 70 and the reference synchronization generation unit 80 may be provided on the external portion of the host terminal 50. For example, it is possible to provide the reference synchronization signal generation unit 80 on the sensor unit side, and the example thereof will be described later with reference to FIG. 7. In addition, the synchronization signal sending unit 70 can be set as a transmitter which is provided on the external portion of the sensor unit group 20 and the host terminal 50.

2. Method of Synchronizing Data from a Plurality of Sensor Units

A method of synchronizing data from the plurality of sensor units 22h, 22g, 23h, and 23g will be described with reference to FIGS. 3 to 6. In FIGS. 3 to 6, N (=four) sensor units 22h, 22g, 23h, and 23g shown in FIGS. 1 and 2 are referred to as a first sensor unit 22h, a second sensor unit 22g, a third sensor unit 23h, and a fourth (N-th) sensor unit 23g.

Figure 3:
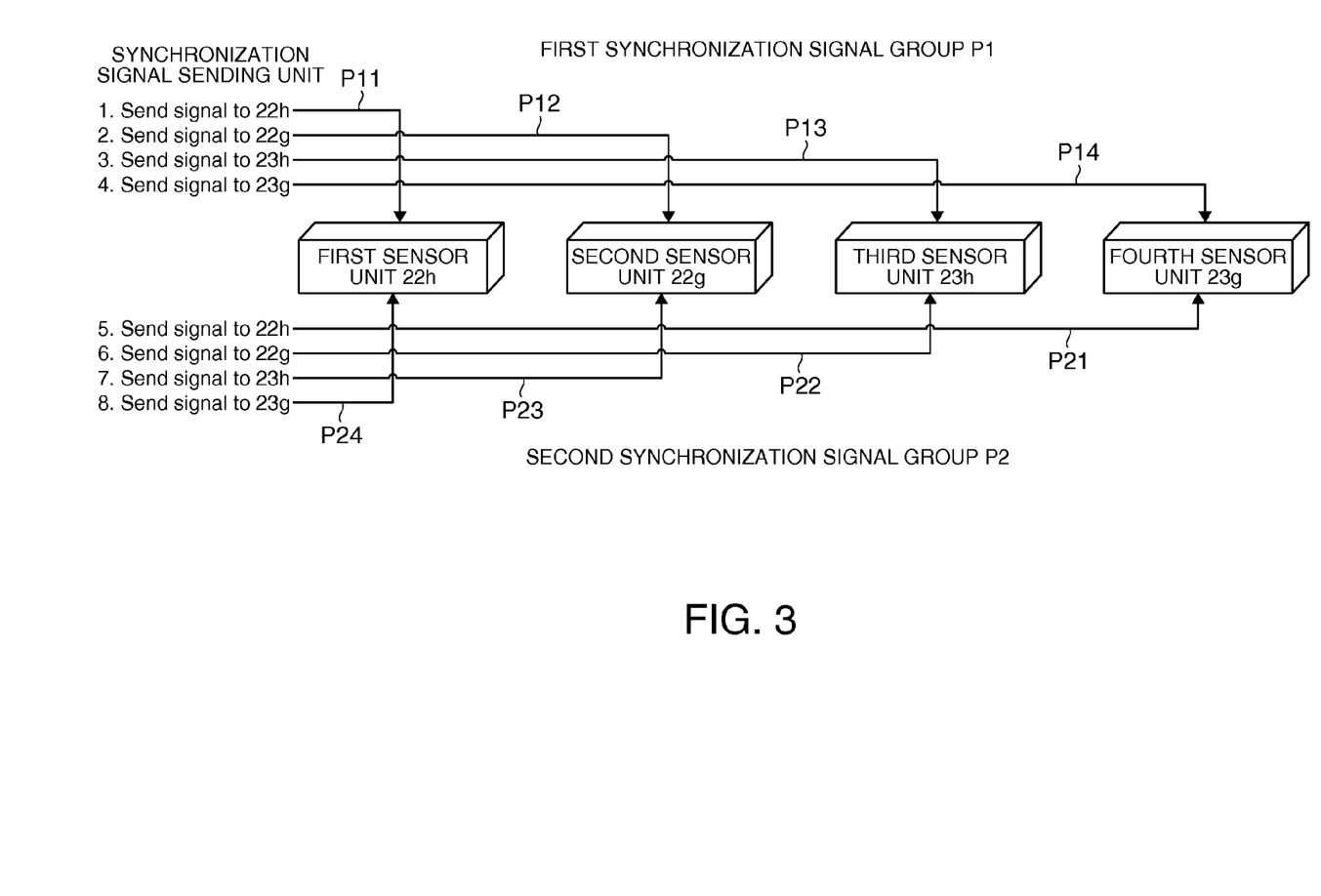
FIG. 3 is a view showing a first synchronization signal group of a forward direction and a second synchronization signal group of a backward direction.

As shown in FIG. 3, the synchronization signal sending unit 70 transmits a synchronization signal group with respect to the communication unit 25 provided in each of the first to fourth sensor units 22h, 22g, 23h, and 23g. This synchronization signal group includes a first synchronization signal group P1 (N first synchronization signals P11, P12, P13, and P14) which is transmitted from the first sensor unit 22h to the fourth sensor unit 23g in a forward direction in chronological order, and a second synchronization signal group P2 (N second synchronization signals P21, P22, P23, and P24) which is transmitted from the fourth sensor unit 23g to the first sensor unit 22h in the backward direction in chronological order.

Figure 4:
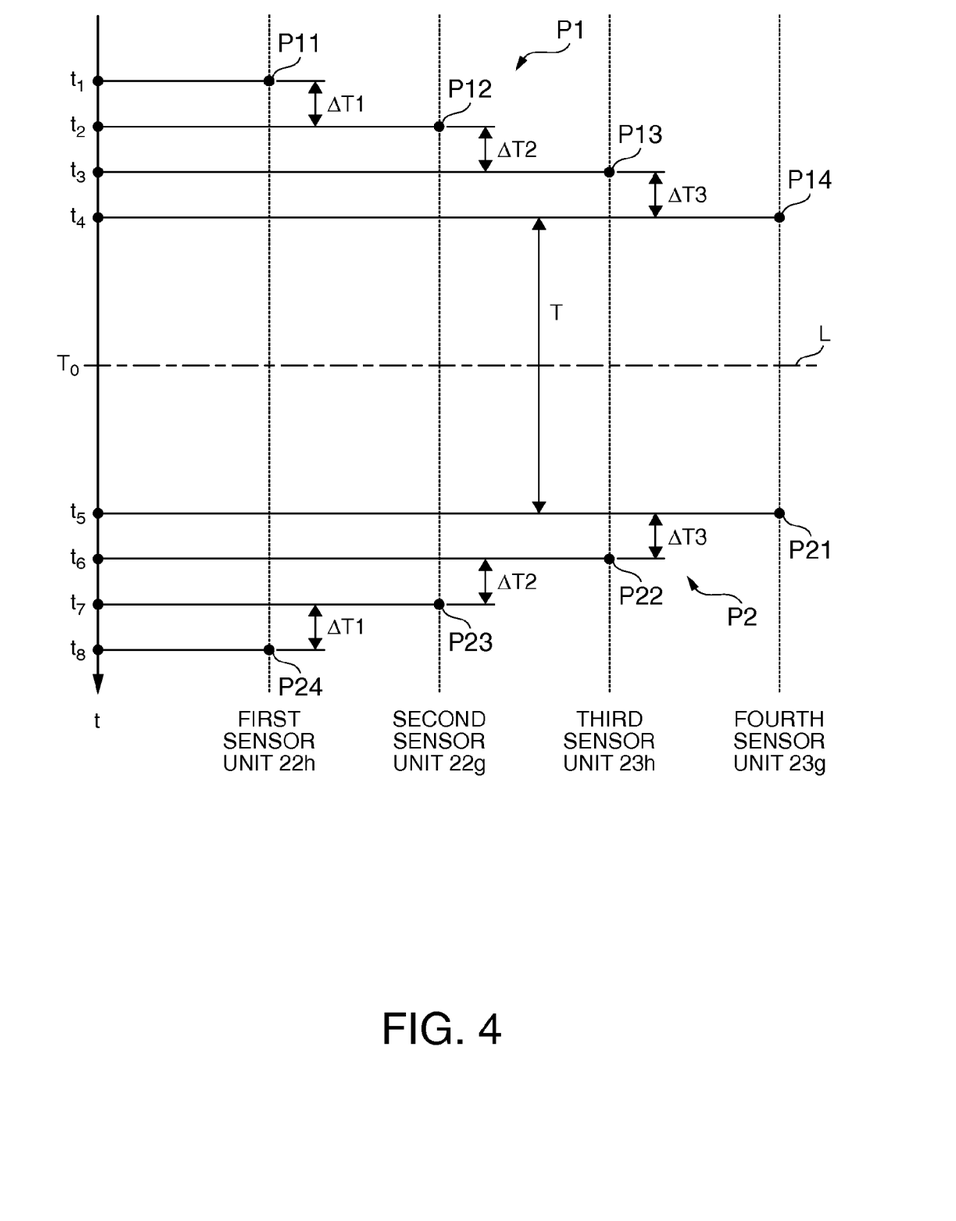
FIG. 4 is a view showing a line-symmetric relationship of first synchronization signal group and second synchronization signal group points plotted on a time axis.

FIG. 4 is a view in which the first synchronization signal group P1 and the second synchronization signal group P2 are plotted on a time axis t. When sending times t1 to t8 of the first synchronization signal group P1 and the second synchronization signal group P2 are plotted on the time axis t, the first synchronization signal group P1 (P11, P12, P13, and P14) and the second synchronization signal group P2 (P21, P22, P23, and P24) are line-symmetrically arranged, with respect to a line L orthogonal to the time axis t which passes a point obtained by bisecting an interval T between the first synchronization signal group P1 and the second synchronization signal group P2.

Herein, in FIG. 4, if t2−t1=ΔT1, t3−t2=ΔT2, and t4−t3=ΔT3, ΔT1=ΔT2=ΔT3. However, it may be ΔT1≠ΔT2≠ΔT3. In this case, in the second synchronization signal group P2, if t6−t5=ΔT3, t7−t6=ΔT2, and t8−t7=ΔT1 are satisfied, the line-symmetric relationship of the first synchronization signal group P1 (P11, P12, P13, and P14) and the second synchronization signal group P2 (P21, P22, P23, and P24) with respect to the line L described above is secured. That is, a sending interval between n-th (1≤n≤N−1) and (n+1)-th synchronization signals of the first synchronization signal group P1 and a sending interval between (N−n)-th and [N−(n−1)]-th synchronization signals of the second synchronization signal group P2 may be equivalent.

As shown in FIG. 3, the synchronization signal P11 transmitted in the forward direction and the synchronization signal P24 transmitted in the backward direction are received by the communication unit 25 of the first sensor unit 22h. In the same manner as described above, the synchronization signals P12 and P23 are received by the second sensor unit 22g, the synchronization signals P13 and P22 are received by the third sensor unit 23h, and the synchronization signals P14 and P21 are received by the fourth sensor unit 23g. In addition, when the host terminal 50 transmits the synchronization signal groups with the Bluetooth standard, the host terminal 50 and each of the first to fourth sensor units 22h, 22g, 23h, and 23g can share a link key in advance, and can set a paring using a pass key when communicating.

In FIG. 1, when the synchronization signal groups are sent in a rest state in which the club 10 is disposed in the club bag 30, for example, it is possible to assume that amounts of reception delay in the first to fourth sensor units 22h, 22g, 23h, and 23g are equivalent. Thus, when the receiving times of the synchronization signals which are received by the first to fourth sensor units 22h, 22g, 23h, and 23g are plotted on the time axis t in the same manner as FIG. 4, it is possible to understand that the line-symmetric relationship of the sent synchronization signal groups is satisfied even at the time of receiving. Thus, in the description hereinafter, the amounts of reception delay is ignored and the times t1 to t8 show both of the sending times and the receiving times.

When the receiving times t1 to t8 are plotted on the time axis t in FIG. 4, it is possible to understand that intermediate times (t8−t1)/2, (t7−t2)/2, (t6−t3)/2, and (t5−t4)/2 which are obtained by bisecting the intervals of each receiving time of two synchronization signals received by the reception unit 25A provided in each of the first to N-th sensor units correspond to time T0 on the line L of FIG. 4 owing to the line-symmetry described above. That is, if the reference synchronization signal is generated at the time T0, it is possible to be used as the reference synchronization signal common in the first to fourth sensor units 22h, 22g, 22h, and 23g. This is a principle which can generate the reference synchronization signal using the first and second synchronization signal groups P1 and P2.

Figure 5:
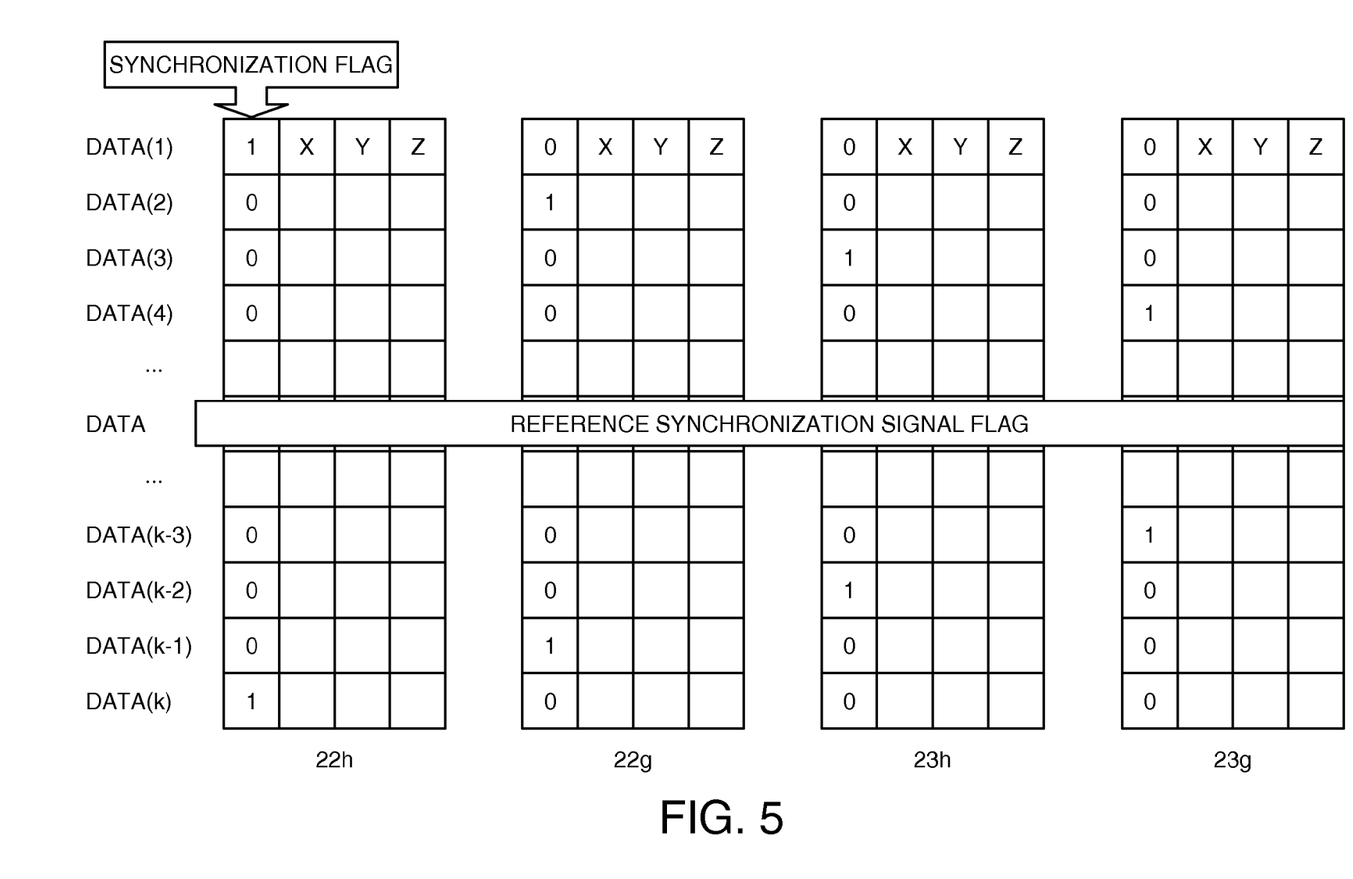
FIG. 5 is a view showing sampling data to which a synchronization flag is set.

FIG. 5 shows a data structure in that the output from the sensor 26 is sampled in a predetermined period in each data processing unit 27 of the first to fourth sensor units 22h, 22g, 23h, and 23g. There is an example of sampling frequency clocks shown in FIG. 5 that correspond to the frequency of the synchronization signal groups of FIG. 4, however it is not limited thereto.

As shown in FIG. 5, a data structure with a bit length suitable for the Bluetooth standard for example, includes X, Y, Z axis sampling data with a predetermined bit length and a synchronization flag bit of a first 1 bit, for example.

In FIG. 5, in the output data from the first sensor unit 22h, a synchronization flag "1" is allocated on each first bit of sampling data (1) corresponding to the receiving time t1 of the synchronization signal P11 and sampling data (k) corresponding to the receiving time t8 of the synchronization signal P24. In the same manner as described above, the synchronization flag "1" is allocated on each first bit of sampling data (2) and (k−1) from the second sensor unit 22g, sampling data (3) and (k−2) from the third sensor unit 23h, and sampling data (4) and (k−3) from the fourth sensor unit 23g. The data processing unit 26 can execute the allocation of the synchronization flag based on the receiving times of the synchronization signals received by the communication unit 25.

The sampling data shown in FIG. 5 is input to the analysis unit 60 of the host terminal 50 through the communication unit 90 of each communication unit 25 of the first to fourth sampling units 22h, 22g, 23h, and 23g.

The reference synchronization signal generation unit 80 provided in the host terminal 50 sets the reference synchronization signal to the sampling data corresponding to the time T0 shown in FIG. 4 from the two sampling data items to which the synchronization flag shown in FIG. 5 is set.

Figure 6:
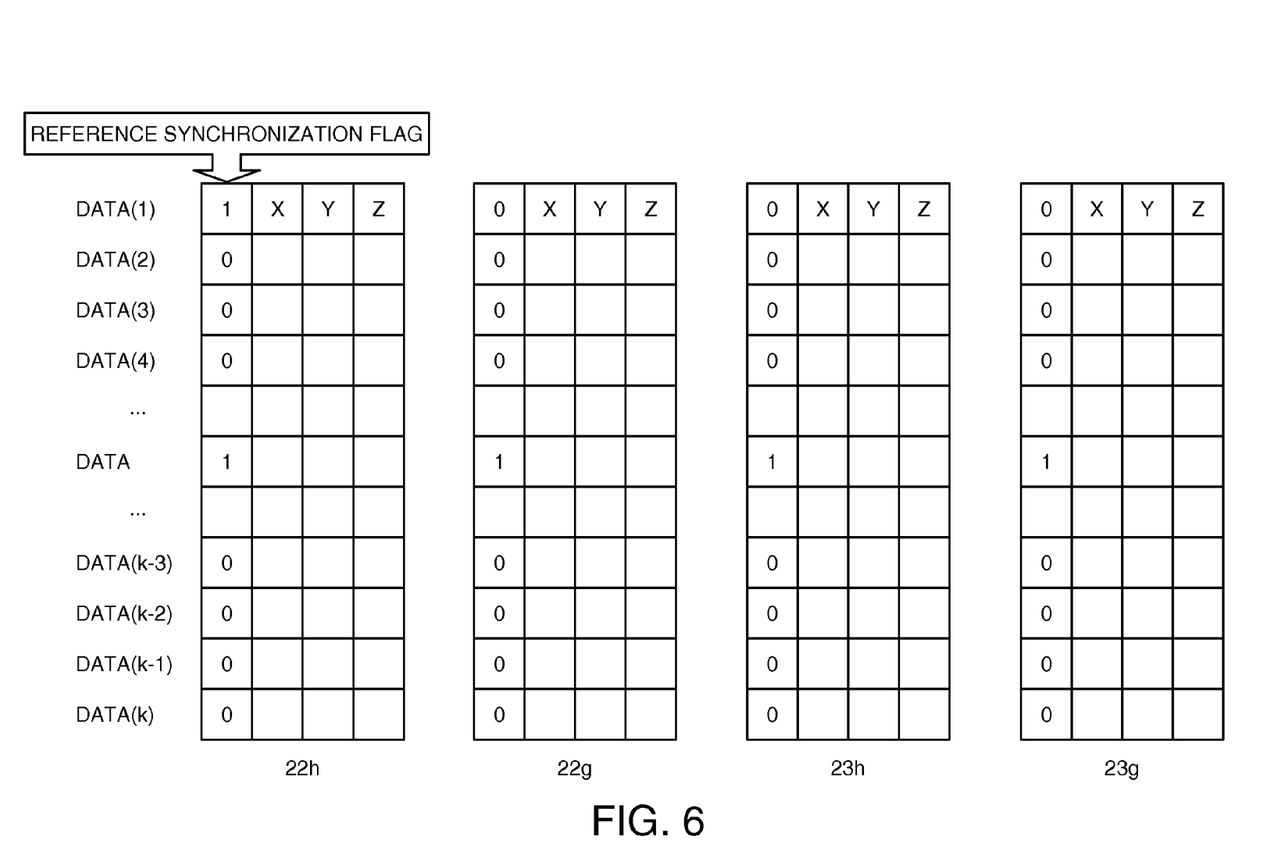
FIG. 6 is a view showing sampling data to which a reference synchronization signal is given.

As an example thereof, the reference synchronization signal generation unit sets the reference synchronization flag "1" to the sampling data corresponding to the receiving time corresponding to the time T0 shown in FIG. 4, as shown in FIG. 6. That is, the reference synchronization signal generation unit 80 sets the reference synchronization flag with respect to each of the plurality of sampling data items obtained from each of the first to fourth sensor units 22h, 22g, 23h, and 23g, which are sampling data corresponding to a center position of two sampling data items set with the synchronization flags.

As described above, a process of calculating from the receiving time of the synchronization signal is not necessary, and the reference synchronization signal generation unit 80 specifies a data position on which the reference synchronization flag is allocated from two synchronization flags. In addition, if total data number k of two sampling data items and the data therebetween is an odd number, the center position between two sampling data items is definitely determined to be in a [(k+1)/2]-th position, and if the total data number k is an even number, the two center position can be any one of (k/2)-th and [(k+2)/2]-th center data. The setting of the reference synchronization flag is executed with respect to output from the first to fourth sensor units 22h, 22g, 23h, and 23g.

The analysis unit 60 can analyze the angular velocity, the angle, the acceleration, velocity, and position at the same time, of each of head portion 11 and grip portion 13 of the club 10 using the sampling data to which the reference synchronization flag is set. This analysis data can be displayed on a display unit of the host terminal 50.

3. Modification Example

The embodiment has been described in detail as described above, however, a person skilled in the art may easily understand that various modifications can be performed in a range without departing from the new matter and the effects of the invention. Accordingly, all of the modification examples are assumed to be included in a range of the invention.

For example, the measurement target object of the invention can be suitably applied to exercise equipment such as a golf club, a tennis racket, or the like; however it is not limited thereto.

Figure 7:
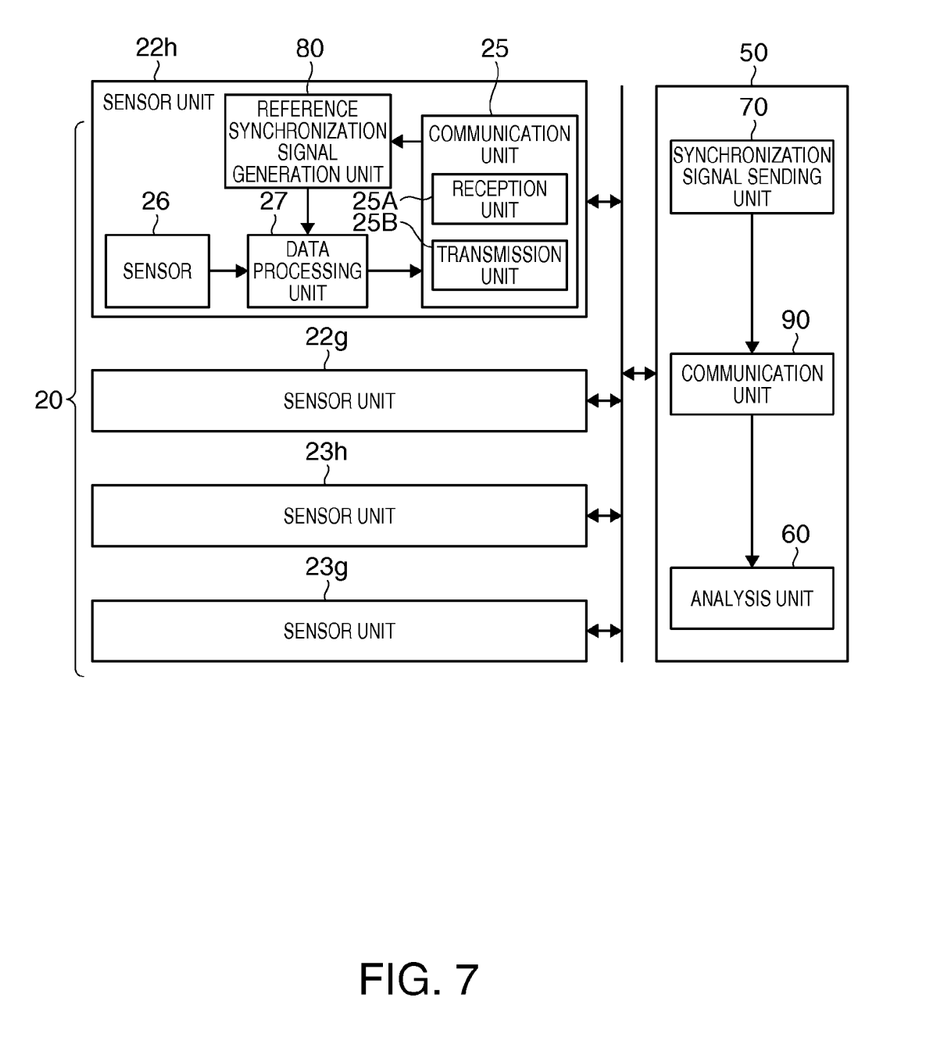
FIG. 7 is a view showing a modification example in which a reference synchronization signal generation unit is provided in each of a plurality of sensor units.

FIG. 7 shows an example of providing the reference synchronization signal generation unit 80 in each of the first to fourth sensor units 22h, 22g, 23h, and 23g. In this case, the data processing unit 50 of each of the plurality of sensor units 22h, 22g, 23h, and 23g can output the sampling data shown in FIG. 6, not FIG. 5. That is, when the reference synchronization signal generation unit 80 is provided in each of the first to fourth sensor units 22h, 22g, 23h, and 23g, instead of the synchronization flag described above, it is possible to set the reference synchronization flag as one of the plurality of sampling data items to be output. At this time, since the data subsequent to the data to which the reference synchronization flag is set is output, it is not necessary to transmit unnecessary data to the host terminal 50.

Figure 8:
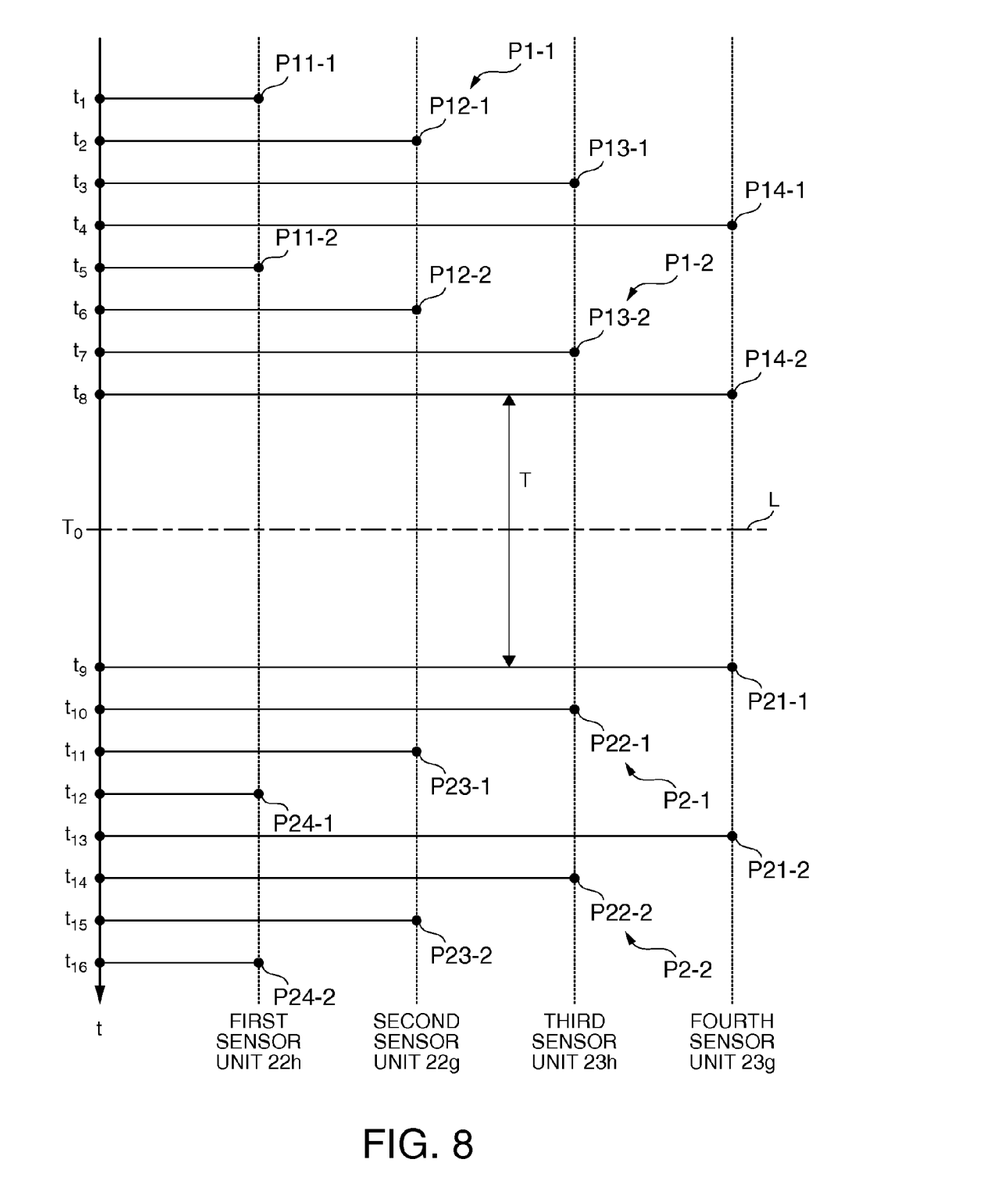
FIG. 8 is a view showing a modification example of transmitting a plurality of pairs of synchronization signal groups when setting first and second synchronization signal groups as a pair of synchronization signal group.

FIG. 8 shows that the reference signal sending unit 70 sends the plurality of pairs of synchronization signal groups (P1-1/P2-1, P1-2/P2-2) when the first synchronization signal group P1 and the second synchronization signal group P2 are set as a pair of synchronization signal group (P1/P2). The reference synchronization signal generation unit 80 can generate the reference synchronization signal at an average intermediate time obtained by averaging the intermediate time obtained from the pair of synchronization signal groups (P1-1/P2-1) and the intermediate times obtained from another pair of the synchronization signal group (P1-2/P2-2) from the plurality of pairs of the synchronization signal groups. Accordingly, it is possible to precisely improve the reference synchronization signal.

In addition, in the embodiment described above, the synchronization signal or the reference synchronization signal is set as the flag in each sampling data, however, in a case of wired connected or the like, for example, the synchronization signal or the reference synchronization signal which is synchronized with the data may be transmitted.

The entire disclosure of Japanese Patent Application No. 2012-011679, filed Jan. 24, 2012 is expressly incorporated by reference herein.

What is claimed is:

1. A motion analysis system for detecting a motion of an object, the system comprising:
    first to N-th sensor units, wherein N is an integer equal to or larger than 2, each of the sensor units is attached to the object, each of the sensor units includes a communication unit that receives and transmits signals, a sensor that outputs sampling data, and a data processing unit that generates a plurality of sampling data items; and
    a host terminal that includes an analysis unit, a synchronization signal sending unit, and a reference synchronization signal generation unit, wherein:
    the synchronization signal sending unit transmits to the communication units of the first to N-th sensor units a first synchronization signal group including N first synchronization signals in order from the first sensor unit to the N-th sensor unit, and transmits a second synchronization signal group including N second synchronization signals in order from the N-th sensor unit to the first sensor unit, such that the synchronization signal sending unit transmits the second synchronization signal group for the first to N-th sensors units in reverse order when compared to a transmission of the first synchronization signal group,
    the plurality of sampling data items generated by the data processing unit includes sample data that is outputted from the sensor and sampled by the data processing unit in chronological order and includes a first and second synchronization flags, the first synchronization flag is associated with a first sampling data sampled at a time in which the communication unit receives the first synchronization signal and the second synchronization flag is associated with a second sampling data sampled at a time in which the communication unit receives the second synchronization signal,
    the data processing unit for a given sensor unit sets the first synchronization flag in response to the receipt of the first synchronization signal by the given sensor unit from the host terminal and sets the second synchronization flag in response to the receipt of the second synchronization signal by the given sensor unit,
    the communication unit transmits the sampling data items to the host terminal,
    the reference synchronization signal generation unit generates a reference synchronization signal which is to be a reference with respect to the first to N-th sensor units,
    the reference synchronization signal generation unit determines an intermediate time by equally dividing a reception interval extending between a reception time of the first synchronization signals and a reception time of the second synchronization signals received by the first to N-th sensor units, wherein the first synchronization flags provided in the sampling data items indicate the reception time of the first synchronization signals and the second synchronization flags provided in the sampling data items indicate the reception time of the second synchronization signals,
    the reference synchronization signal generation unit sets a reference synchronization flag at the intermediate time and the sampling data taken at the intermediate time is associated with the reference synchronization signal, and
    the analysis unit analyzes a motion of the object based on the sampling data items and the reference synchronization flag.

2. The motion analysis system according to claim 1, wherein, in the first synchronization signal group and the second synchronization signal group, points as plotted sending times on a time axis are line-symmetric with respect to a line orthogonal to the time axis which passes a point obtained by bisecting an interval between the first synchronization signal group and the second synchronization signal group.

3. The motion analysis system according to claim 2, wherein a sending interval between n-th ($1 \leq n \leq N-1$) and (n+1)-th synchronization signals of the first synchronization signal group and a sending interval between (N−n)-th and [N−(n−1)]-th synchronization signals of the second synchronization signal group are equivalent.

4. The motion analysis system according to claim 1, wherein the synchronization signal sending unit sends a plurality of pairs of synchronization signal groups when setting the first synchronization signal group and the second synchronization signal group as a pair of synchronization signal groups, and the reference synchronization signal generation unit determines an average intermediate time obtained by averaging the intermediate times which are obtained from pair of synchronization signal groups from the plurality of pairs of the synchronization signal groups.

5. A motion analysis method for obtaining a plurality of sampling data items output from a first to N-th sensor units attached to an object, to analyze a motion of the object, where N is an integer equal to or larger than 2, the method comprising:

transmitting, by a host terminal, a first synchronization signal group including N first synchronization signals in order from the first sensor unit to the N-th sensor unit, wherein the host terminal is separate from the object, and each of the sensor units includes a communication unit that receives a respective first synchronization signal, a sensor that outputs sample data, and a data processing unit that generates the plurality of sampling data items;

transmitting, by the host terminal, a second synchronization signal group including N second synchronization signals in order from the N-th sensor unit to the first sensor unit, wherein the communication unit of each sensor unit receives a respective second synchronization signal;

setting, by each of the sensor units, a first synchronization flag in response to the receipt of the first synchronization signal by a given sensor unit from the host terminal and a second synchronization flag in response to the receipt of the second synchronization signal by the given sensor unit;

transmitting, by each of the sensor units, the sampling data items to the host terminal, wherein the plurality of sampling data items generated by the data processing unit includes sample data that is outputted from the sensor and sampled by the data processing unit in chronological order and includes the first and second synchronization flags, the first synchronization flag is associated with a first sampling data sampled at a time in which the sensor unit receives the first synchronization signal and the second synchronization flag is associated with a second sampling data sampled at a time in which the sensor unit receives the second synchronization signal;

determining, by the host terminal, an intermediate time by equally dividing a reception interval extending between a reception time of the first synchronization signals and a reception time of the second synchronization signals received by the first to N-th sensor units;

setting, by the host terminal, a reference synchronization flag at the intermediate time and associating, by the host terminal, the sampling data taken at the intermediate time with a reference synchronization signal; and analyzing, by the host terminal, a motion of the object based on the sampling data items and the reference synchronization flag.

* * * * *